United States Patent [19]
Thiem et al.

[11] Patent Number: 5,891,854
[45] Date of Patent: Apr. 6, 1999

[54] COSMETIC FORMULATIONS HAVING AN EFFECTIVE CONTENT OF GLYCOSYL GLYCERIDES

[75] Inventors: Joachim Thiem; Oliver Scheel; Günther Schneider, all of Hamburg, Germany

[73] Assignee: Beiersdorf AG, Hamburg, Germany

[21] Appl. No.: 736,147

[22] Filed: Oct. 24, 1996

[30] Foreign Application Priority Data

Nov. 2, 1995 [DE] Germany ............ 195 40 749.0

[51] Int. Cl.⁶ .................. A61K 31/70; A61K 31/715; C07H 15/04; C07H 3/00; C07G 3/00
[52] U.S. Cl. ...................... 514/25; 514/53; 536/4.1; 536/120
[58] Field of Search ............... 514/25, 53; 536/120, 536/4.1

[56] References Cited

U.S. PATENT DOCUMENTS 5,006,337  4/1991  Motitschke et al. ............ 424/195.1

FOREIGN PATENT DOCUMENTS 550280   7/1993   European Pat. Off. .
9625142  4/1996   WIPO .

OTHER PUBLICATIONS

JACOS vol. 69, No. 4, issued Apr. 1992, Prieto et al., "Optimized Separation of Nonpolar and Polar Lipid Classes from Wheat Flour by Solid–Phase Exraction" pp. 387–391.
Grant & Hackh's Chemical Dictionary, 5th edition, published 1987 by McGraw–Hill.
Patent Abstracts of Japan, vol. 8, No. 145, Abstract of JP 01–67,237 (1989); Patent No. –JP59053497 84.03.28.
Patent Abstracts of Japan, vol. 13, No. 273, Abstract of JP 001–67,237 (1989).

*Primary Examiner*—Marian C. Knode
*Assistant Examiner*—Everett White
*Attorney, Agent, or Firm*—Sprung Kramer Schaefer & Briscoe

[57] ABSTRACT

Cosmetic ceutical formulations characterized by an effective, content of pharmaceutically and/or cosmetically unobjectionable hexosyl glycerides and/or (hexosyl)hexosyl glycerides.

16 Claims, No Drawings

COSMETIC FORMULATIONS HAVING AN EFFECTIVE CONTENT OF GLYCOSYL GLYCERIDES

The present invention relates to new active compounds, to their preparation and to their use in the field of cosmetic and pharmaceutical dermatology. The present invention relates in particular to active compounds pounds and to cosmetic or dermatological formulations comprising such active-compound combinations. In particular, the present invention relates to cosmetic formulations having a content of substances which increase skin moistness.

The outermost layer of the epidermis, the stratum corneum (horny cell layer) is, as an important barrier layer, of particular importance for, inter alia, protection against environmental influences and against drying out. In contact with the environment, the horny cell layer is continually worn down and must therefore constantly be renewed.

A model of the skin which is currently widespread in the technical field perceives the stratum corneum as a two-component system similar to a brick wall (bricks-and-mortar model). In this model, the corneocytes (horny cells) correspond to the bricks, while the lipid membrane in the intercellular spaces, which is of complex composition, corresponds to the mortar.

Apart from their barrier effect towards external chemical and physical influences, the epidermal lipids also correspond to the cohesion of the horny cell layer and exert influence over the smoothness of the skin. In contrast to the sebaceous-gland lipids, which do not form a coherent film over the skin, the epidermal lipids are distributed over the entire horny cell layer.

The extremely complex interaction of the moisture-binding substances and of the lipids of the upper skin layers is very important for the regulation of skin moistness. For this reason, cosmetics generally contain not only balanced blends of lipids, and water, but also water-binding substances. These include polyols such as glycerol, sorbitol and xylitol, ethoxylated polyols, and hydrolysed proteins. Use is also made of the substances present in the natural moisturizing factor (NMF) such as, for example, urea, carbohydrates (e.g. glucose) and amino acids (e.g. serine). These substances are therefore of particular importance for the care function of a cosmetic product, for reasons including, in particular, their relatively good compatibility with the skin and mucous membranes.

A problem which remains unresolved, however, is that even the substances glucose and glycerol, which in principle are entirely unobjectionable, may give rise in particularly sensitive individuals and at very high levels to certain symptoms of irritation to the skin and mucous membranes. The aim was therefore to find moisture-providing substances (moisturizers) possessing an even better compatibility than, for example, glucose and glycerol.

It was surprising, and for the skilled worker unforeseeable, that cosmetic or pharmaceutical formulations characterized by an effective content of pharmaceutically and/or cosmetically unobjectionable hexosyl glycerides and/or (hexosyl)hexosyl glycerides remedy the disadvantages of the prior art.

The hexoses on which the novel hexosyl glycerides are based are preferably selected from the group of the aldohexoses, usually in their pyranoid form, i.e. allo(pyrano) se, altro(pyrano) se, gluco(pyrano) se, manno(pyrano)se, gulo(pyrano) se, ido(pyrano)se, galacto(pyrano)se and talo (pyrano)se.

The (hexosyl)hexoses on which the novel (hexosyl) hexosyl glycerides are based can be selected from the group of pyranosylpyranoses and furanosylpyranoses with a 1,4-glycosidic or 1,6-glycosidic linkage. They are preferably selected from the group consisting of maltose, leucrose and lactose.

Accordingly, the novel hexosyl glycerides can be denoted by the general structural formulae

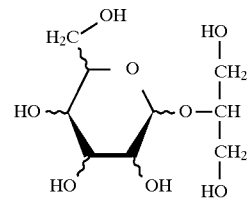

or

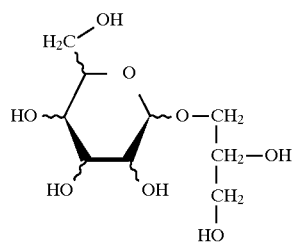

and the novel (hexosyl)hexosyl glycerides by the general structural formulae

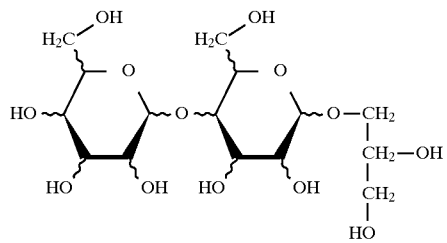

or

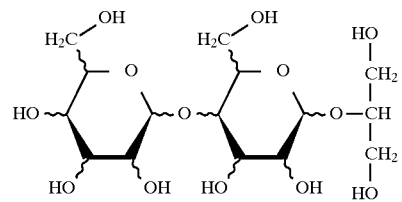

or

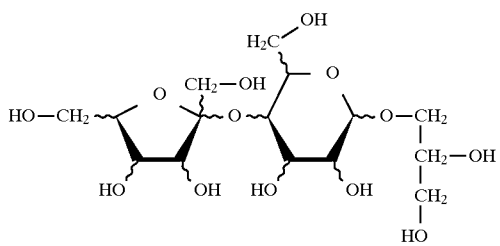

or

-continued

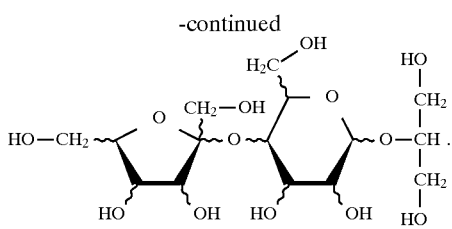

It is advantageous to employ D-hexosyl glycosides, although L-hexosyl glycosides can also be used with advantage in the context of the present invention.

Moreover, hexosyl glycerides based on D- or L-ketohexoses, i.e. psicose, fructose, sorbose or tagatose, commonly present in their furanoid form, can if desired be employed with advantage in the context of the present invention.

Glucosyl glycerides of the general formula

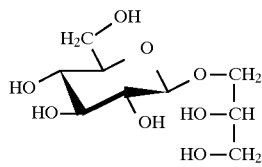

and/or of the general formula

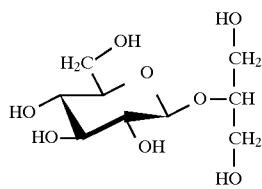

and/or of the general formula

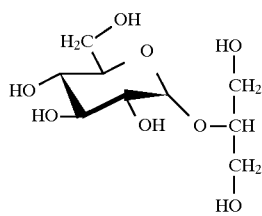

and/or of the general formula

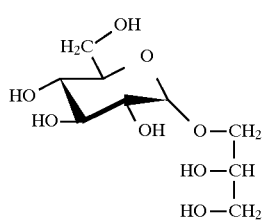

are preferred in accordance with the invention.

A particularly preferred hexosyl glyceride is (2-O-β-D-glucopyranosyl)-sn-glycerol.

It was therefore not foreseeable for the skilled worker that the novel glycosyl glycerides and cosmetic or dermatological formulations comprising them act better as a moisturizing agent and act better against skin ageing than the active compounds, active-compound combinations and formulations of the prior art.

The novel cosmetic or dermatological formulations can have the customary composition and can be used for the treatment, care and cleansing of the skin and/or hair and as a make-up product in decorative cosmetics. They contain preferably from 0.001% by weight to 10% by weight, but in particular from 0.01% by weight to 6% by weight, based on the overall weight of the composition, of the novel glycosyl glycerides.

For use, the novel cosmetic and dermatological formulations are applied to the skin and/or hair in sufficient quantity in the manner customary for cosmetics.

Novel cosmetic and dermatological formulations can exist in various forms. Thus they may constitute, for example, a solution, a nonaqueous formulation, an emulsion or microemulsion of the water-in-oil (W/O) or oil-in-water (O/W) type, a multiple emulsion, for example of the water-in-oil-in-water (W/O/W) type, a gel, a hydrodispersion, a solid stick, an ointment or else an aerosol. It is also advantageous to offer the novel glycosyl glycerides in encapsulated form, encapsulated for example in collagen matrices and other common encapsulating materials, for example as cellulose capsules or encapsulated in gelatin, wax matrices or liposomally.

It is also possible and advantageous in the context of the present invention to introduce the novel glycosyl glycerides into aqueous systems and surfactant formulations for cleansing the skin and hair.

The novel cosmetic and dermatological formulations may include cosmetic auxiliaries as are commonly used in such formulations, examples being preservatives, bactericides, perfumes, substances for preventing foaming, dyes, pigments having a colouring action, thickeners, surfactants, emulsifiers, softening, moisturizing and/or moisture-retaining substances, fats, oils, waxes or other customary constituents of a cosmetic or dermatological formulation, such as alcohols, polyols, polymers, foam stabilizers, electrolytes, organic solvents or silicone derivatives.

In particular, the novel glycosyl glycerides can also be combined with other antioxidants.

In accordance with the invention, favourable antioxidants which can be used are all antioxidants which are appropriate or customary for cosmetic and/or dermatological applications.

The antioxidants are advantageously chosen from the group consisting of amino acids (e.g. glycine, histidine, tyrosine, tryptophan) and their derivatives, imidazoles (e.g. urocanic acid) and derivatives thereof, peptides such as D,L-carnosine, D-carnosine, L-carnosine and derivatives thereof (e.g. anserine), carotenoids, carotenes (e.g. a-carotene, β-carotene, lycopene) and derivatives thereof, chlorogenic acid and derivatives thereof, liponic acid and derivatives thereof (e.g. dihydroliponic acid) aurothioglucose, propylthiouracil and other thioles (e.g. thioredoxin, glutathione, cysteine, cystine, cystamine and their glycosyl, Nacetyl, methyl, ethyl, propyl, amyl, butyl and lauryl, palmitoyl, oleyl, γ-linoloyl, cholesteryl and glyceryl esters) and salts thereof, dilauryl thiodipropionate, distearyl thiodipropionate, thiodipropionic acid and derivatives thereof (eaters, ethers, peptides, lipids, nucleotides, nucleosides and salts) and also sulphoximine compounds (e.g. buthionine-sulphoximines, homocysteine-sulphoximine, buthionine sulphones, penta-, hexa- and heptathionine-sulphoximine) in very low compatible doses (e.g. pmol to μmol/kg), and also (metal) chelators (e.g.

α-hydroxy fatty acids, palmitic acid, phytic acid, lactoferrin), α-hydroxy acids (e.g. citric acid, lactic acid, malic acid), humic acid, bile acid, bile extracts, ilirubin, biliverdin, EDTA, EGTA and derivatives theref, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palpitate, Mg ascorbyl phosphate, ascorbyl acetate), tocopherols and derivatives (e.g. vitamin E acetate), vitamin A and derivatives (vitamin A palpitate) and also coniferyl benzoate of benzoin resin, rutic acid and derivatives thereof, α-glycosyl rutin, ferulic acid, furfurylideneglucitol, carnosine, butylated hydroxytoluene, butylhydroxyanisole, nordihydroguaiac resin acid, nordihydroguaiaretic acid, trihydroxybutyrophenone, uric acid and derivatives thereof, mannose and derivatives thereof, zinc and its derivatives (e.g. ZnO, $ZnSO_4$), selenium and its derivatives (e.g. selenium methionine), stilbenes and derivatives thereof (e.g. stilbene oxide, trans-stilbene oxide) and the derivatives (salts, esters, ethers, sugars, nucleotides, nucleosides, peptides and lipids) of these active compounds mentioned which are suitable according to the invention.

The quantity of the abovementioned antioxidants (one or more compounds) in the novel formulations is preferably from 0.001 to 30% by weight, particularly preferably 0.05–20% by weight, in particular 1–10% by weight, based on the overall weight of the formulation.

If vitamin E and/or its derivatives constitute the antioxidant or antioxidants, it is advantageous to choose the particular concentrations thereof from the range 0.001–10% by weight, based on the overall weight of the formulation.

If vitamin A and/or its derivatives, and/or carotenes and/or their derivatives, constitute the antioxidant or antioxidants, it is advantageous to choose the particular concentrations thereof from the range 0.001–10% by weight, based on the overall weight of the formulation.

Novel emulsions are advantageous and contain, for example, the abovementioned fats, oils, waxes and other fatty substances, and also water and an emulsifier as is commonly employed for such a type of formulation.

In this case the lipid phase can advantageously be chosen from the following group of substances:

natural, synthetic and/or semisynthetic oils, such as triglycerides of capric or of caprylic acid, but preferably castor oil;

fats, waxes and other natural, synthetic and/or semisynthetic fatty substances, preferably esters of fatty acids with alcohols of low carbon number, for example with isopropanol, propylene glycol or glycerol, or esters of fatty alcohols with alkanoic acids of low carbon number or with fatty acids;

silicone oils such an dimethylpolysiloxane, diethylpolysiloxane, diphenylpolysiloxanes and mixed forms thereof; and saturated compounds such as hydrocarbons of natural or synthetic origin (petroleum jelly, squalane).

The aqueous phase of the novel formulations advantageously includes, if desired, alcohols, diols or polyols of low carbon number, and their ethers, preferably ethanol, isopropanol, propylene glycol, glycerol, ethylene glycol, ethylene glycol monoethyl or monobutyl ether, propylene glycol monomethyl, monoothyl or monobutyl other, diethylene glycol monomethyl or monoethyl ether and analogous products, and also, in particular, one or more thickeners which can advantageously be chosen from the group consisting of silica, aluminium silicates, polysaccharides and derivatives thereof, for example hyaluronic acid, xanthan gum, hydroxypropylmethylcellulose, particularly advantageously from the group consisting of polyacrylates, preferably a polyacrylate from the group of the so-called Carbopols, for example Carbopols of type 980, 981, 1382, 2984, 5984, in each case individually or in combination.

In particular, mixtures of the abovementioned solvents are used. In the case of alcoholic solvents, water may be an additional constituent.

Gels according to the invention normally contain alcohols of low carbon number, for example ethanol, isopropanol, 1,2-propanediol, glycerol and water, or an abovementioned oil in the presence of a thickener which in the case of oily-alcoholic gels is preferably silica or an aluminium silicate, while in the case of aqueousalcoholate or alcoholate gels it is preferably a polyacrylate.

Suitable propellants for novel formulations which can be sprayed from aerosol containers are the customary, known, highly volatile liquefied propellants, for example hydrocarbons (propane, butane, isobutane), which can be employed alone or in a mixture with one another. Compressed air can also be used with advantage.

Novel formulations may additionally and advantageously contain substances which absorb UV radiation in the UVB range, the overall quantity of the screening substances being, for example, from 0.1% by weight to 30% by weight, preferably from 0.5 to 10% by weight, in particular from 1.0 to 6.0% by weight, based on the overall weight of the formulations, in order to provide cosmetic formulations which protect the hair and/or the skin against the entire range of ultraviolet radiation. They can also be used as sun protection compositions for the hair or skin.

If the novel emulsions contain UVB screening substances, these can be oil-soluble or water-soluble. Examples of advantageous oil-soluble UVB screening agents in accordance with the invention are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino) benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di(2-ethylhexyl 4-methoxybenzalmalonate, 2,4,6-trianilino)p-carbo-2'-ethyl-1'-hexyloxy)-1,3,5-triazine.

Examples of advantageous water-soluble uVB screening agents are:

salts of 2-phenylbenzimidazole-5-sulphonic acid, such as its sodium, potassium or its triethanolammonium salt, and the sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl) benzenesulphonic acids, 2-methyl-5-(2-oxo-3-bornylidenemethyl)sulphonic acid and salts thereof.

The list of the abovementioned UVB screening agents which can be used in combination with the novel glycosyl glycerides is of course not intended to be limiting.

It can also be advantageous to combine novel glycosyl glycerides with UVA screening agents which have to date been customarily present in cosmetic formulations. These substances are preferably derivatives of dibenzoylmethane, especially 1-(4'-tert-butylphenyl)-3-(4'-methoxyphenyl) propane-1,3-dione and 1-phenyl3-(4'-isopropylphenyl) propan-1,3-dione. These combinations or formulations containing these combinations are also part of the invention. The quantities which can be employed are those used for the UVB combination.

The invention additionally relates to the use of a combination of the novel glycosyl glycerides with at least one UVA screening agent as antioxidant and to the use of a combination of the novel glycosyl glycerides with at least one UVA screening agent as antioxidant in a cosmetic or dermatological formulation.

The invention additionally relates to the use of a combination of the novel glycosyl glycerides with at least one UVA screening agent and at least one UVB screening agent as antioxidant and to the use of a combination of the novel glycosyl-glycerides with at least one UVA screening agent and at least one UVB screening agent as antioxidant in a cosmetic or dermatological formulation.

Cosmetic and dermatological formulations having an effective content of novel glycosyl glycerides may also include inorganic pigments which are customarily used in cosmetics to protect the skin against UV rays. These pigments are oxides of titanium, of zinc, of iron, of zirconium, of silicon, of manganese, of aluminium and of cerium and of mixtures thereof, and modifications in which the oxides are the active agents. With particular preference they are pigments based on titanium dioxide.

The invention also relates to these combinations of UVA screening agent and pigment and to formulations containing this combination. The quantities which can be used are those specified for the abovementioned combinations.

Cosmetic and dermatological formulations for protecting the hair against UV rays in accordance with the invention are, for example, shampoo compositions, formulations employed in the course of rinsing the hair before or after shampooing, before or after permanent wave treatment, before or after dyeing or bleaching of the hair, or formulations for blow drying or setting the hair, formulations for dyeing or bleaching, or a hair lotion and treatment lotion, a hair lacquer or a permanent-wave composition.

The cosmetic and dermatological formulations include active compounds and auxiliaries as are commonly used for this type of formulation for hair care and hair treatment. Auxiliaries used are preservatives, surfactants, substances for reducing foaming, thickeners, emulsifiers, fats, oils, waxes, organic solvents, bactericides, fragrances, dyes or pigments whose function is to colour the hair or the cosmetic or dermatological formulation itself, electrolytes and substances to act against the hair becoming greasy.

The term electrolytes in the context of the present invention refers to water-soluble alkali metal solvents, ammonium salts, alkaline earth metal salts (including magnesium) and zinc salts with inorganic anions and any desired mixtures of such salts, it being necessary to ensure that these salts are pharmaceutically or cosmetically unobjectionable.

The novel anions are preferably selected from the group consisting of chlorides, sulphates and hydrogen sulphates, phosphates, hydrogen phosphates and linear and cyclic oligophosphates, and also carbonates and hydrogen carbonates.

Cosmetic formulations in the form of a skin cleansing composition or shampoo composition preferably include at least one anionic, nonionic or amphoteric surfactant, or else mixtures of such surfactants, novel glycosyl glycerides in an aqueous medium, and auxiliaries as are customarily used therefor. The surfactant or mixtures thereof can be present in a concentration of between 1% by weight and 50% by weight in the shampoo composition.

If the cosmetic or dermatological formulations are in the form of a lotion which is rinsed out and applied,. for example, before or after bleaching, before or after shampooing, between two shampooing steps, or before or after permanent-wave treatment, then these formulations are, for example, aqueous or aqueousalcoholic solutions which, if desired, contain surfactants whose concentration may be between 0.1 and 10% by weight, preferably between 0.2 and 5% by weight.

These cosmetic or dermatological formulations may also constitute aerosols containing the auxiliaries commonly used for such formulations.

A cosmetic formulation in the form of a lotion which is not rinsed out, especially a hair-setting lotion, a lotion which is used in the course of blow drying the hair, or a hair lotion and treatment lotion, is generally an aqueous, alcoholic or aqueous-alcoholic solution and includes at least one cationic, anionic, nonionic or amphoteric polymer or else mixtures thereof, and also novel active-compound combinations in an effective concentration. The quantity of the polymers used is, for example, between 0.1 and 10% by weight, preferably between 0.1 and 3% by weight.

Cosmetic formulations for treatment and care of the hair, which contain novel glycosyl glycerides, can be present as emulsions of the nonionic or anionic type. Nonionic emulsions contain, in addition to water, oils or fatty alcohols which may, for example, also be polyethoxylated or polypropoxylated, or else mixtures of the two organic components. These emulsions contain, if desired, cationic surfactants.

In accordance with the invention it is possible for cosmetic formulations for the treatment and care of the hair to be present as gels which in addition to an effective content of novel glycosyl glycerides and solvents, preferably water, commonly used for this purpose, also contain organic thickeners, for example gum arabic, xanthan gum, sodium alginate, cellulose derivatives, preferably methylcellulose, hydroxymethylcellulose, hydroxyethylcellulose, hydroxypropylcellulose, hydroxypropylmethylcellulose or inorganic thickeners, for example aluminium silicates such as, for example, bentonites, or a mixture of polyethylene glycol and polyethylene glycol stearate or distearate. The thickener is present in the gel, for example, in a quantity of between 0.1 and 30% by weight, preferably between 0.5 and 15% by weight.

The quantity of the novel glycosyl glycerides in a composition intended for the hair is preferably from 0.05% by weight to 10% by weight, in particular from 0.5% by weight to 5% by weight, based on the overall weight of the composition.

Novel aqueous cosmetic cleansing compositions, or concentrated cleansing compositions with a low or zero content of water which are intended for aqueous cleansing, may contain anionic, nonionic and/or amphoteric surfactants, examples being
conventional soaps, for example fatty acid salts of sodium alkyl sulphates, alkyl ether sulphates, alkane- and alkylbenzenesulphonates
sulphoacetates
sulphobetaines
sarcosinates amidosulphobetaines
sulphosuccinates
sulphosuccinic monoesters
alkyl ether carboxylates
protein-fatty acid condensates
alkylbetaines and amidobetaines
fatty acid alkanolamides
polyglycol ether derivatives Cosmetic formulations which constitute cosmetic cleansing formulations for the skin can be present in liquid or solid form. In addition to novel glycosyl glycerides they preferably include at least one anionic, nonionic or amphoteric surf actant or mixtures thereof, if desired one or more electrolytes, and auxiliaries as are commonly used for such formulations. The surfactant can be present in a concentration of between 1 and 94% by weight in the cleansing formulations, based on the overall weight of the formulations.

Cosmetic formulations which constitute a shampoo composition include, in addition to an effective content of novel glycosyl glycerides, preferably at least one anionic, nonionic or amphoteric surfactant or mixtures thereof, if desired a novel electrolyte, and auxiliaries as are commonly used for such formulations. The surfactant can be present in the shampoo composition in a concentration of between 1% by weight and 94% by weight.

In addition to the abovementioned surfactants, the novel compositions include water and, if desired, the additives customary in cosmetics, examples being fragrance, thickeners, dyes, deodorants, antimicrobial substances, re-oiling agents, complexing agents and sequestering agents, pearlescence agents, plant extracts, vitamins, active compounds and the like.

The invention also relates to the process for producing the novel cosmetic compositions, which is characterized in that novel glycosyl glycerides are incorporated in a manner known per se into cosmetic and dermatological formulations.

The examples which follow are intended to illustrate the present invention without limiting it. The preparation set out in Examples 1–3, of the peracetates of the oligosaccharides, the peracetates of the glycosyl glycerides and, ultimately, of the glycosyl glycerides themselves, can be applied mutatis mutandis to all novel glycosyl glycerides and their precursors.

| Example 1: | % by wt. |
|---|---|
| Sorbitol stearate | 2.50 |
| Petroleum jelly | 1.50 |
| Liquid paraffin, subliquidum | 10.00 |
| Octyldodecanol | 4.00 |
| Hydrogenated coconut fatty acid glycerides | 2.00 |
| Carbomer 2984 | 0.20 |
| Cetyl phosphate | 0.10 |
| (2-O-β-D-Glucopyranosyl)-sn-glycerol | 2.00 |
| Fragrance, preservatives, dyes, antioxidants | q.s. |
| Water | to 100.00 |

| Example 2: | % by wt. |
|---|---|
| Sorbitol stearate | 2.50 |
| Petroleum jelly | 1.50 |
| Liquid paraffin, subliquidum | 10.00 |
| Octyldodecanol | 4.00 |
| Hydrogenated coconut fatty acid glycerides | 2.00 |
| Carbomer 2984 | 0.20 |
| Cetyl phosphate | 0.10 |
| (2-O-β-D-Glucopyranosyl)-sn-glycerol | 2.00 |
| Serine | 2.00 |
| Fragrance, preservatives, dyes, antioxidants | q.s. |
| Water | to 100.00 |

| Example 3: | % by wt. |
|---|---|
| Sorbitol stearate | 2.50 |
| Petroleum jelly | 1.50 |
| Liquid paraffin, subliquidum | 10.00 |
| Octyldodecanol | 4.00 |
| Hydrogenated coconut fatty acid glycerides | 2.00 |
| Carbomer 2984 | 0.20 |
| Cetyl phosphate | 0.10 |
| (2-O-β-D-Glucopyranosyl)-sn-glycerol | 2.00 |
| Trehalose | 2.00 |
| Fragrance, preservatives, dyes, antioxidants, etc. | |
| Water | to 100.00 |

| Example 4: | % by wt. |
|---|---|
| Sorbitol stearate | 2.50 |
| Petroleum jelly | 1.50 |
| Liquid paraffin, subliquidum | 10.00 |
| Octyldodecanol | 4.00 |
| Hydrogenated coconut fatty acid glycerides | 2.00 |
| Carbomer 2984 | 0.20 |
| Cetyl phosphate | 0.10 |
| (2-O-β-D-Glucopyranosyl)-sn-glycerol | 2.00 |
| Glycerol | 2.00 |
| Fragrance, preservatives, dyes, antioxidants | q.s. |
| Water | to 100.00 |

| Example 5: | % by wt. |
|---|---|
| Sorbitol stearate | 2.50 |
| Petroleum jelly | 1.50 |
| Liquid paraffin, subliquidum | 10.00 |
| Octyldodecanol | 4.00 |
| Hydrogenated coconut fatty acid glycerides | 2.00 |
| Carbomer 2984 | 0.20 |
| Cetyl phosphate | 0.10 |
| (2-O-β-D-Glucopyranosyl)-sn-glycerol | 2.00 |
| Trehalose | 2.00 |
| Serine | 2.00 |
| Fragrance, preservatives, dyes, antioxidants | q.s. |
| Water | to 100.00 |

| Example 6: | % by wt. |
|---|---|
| Sorbitol stearate | 2.50 |
| Petroleum jelly | 1.50 |
| Liquid paraffin, subliquidum | 10.00 |
| Octyldodecanol | 4.00 |
| Hydrogenated coconut fatty acid glycerides | 2.00 |
| Carbomer 2984 | 0.20 |
| Cetyl phosphate | 0.10 |
| (2-O-β-D-Glucopyranosyl)-sn-glycerol | 2.00 |
| Panthenol | 1.00 |
| Tocopherol acetate | 1.50 |
| Bisabolol | 0.10 |

| Example 6: | % by wt. |
|---|---|
| Fragrance, preservatives, dyes, antioxidants | q.s. |
| Water | to 100.00 |

| Example 7: | % by wt. |
|---|---|
| PEG 8 (polyethylene glycol 400) | 5.00 |
| Ethanol | 1.00 |
| (2-O-β-D-Glucopyranosyl)-sn-glycerol | 1.50 |
| Carbomer 2984 | 0.70 |
| Fragrance, preservatives, dyes, antioxidants, etc. | q.s. |
| Water | to 100.00 |

| Example 8: | % by wt. |
|---|---|
| PEG 8 (polyethylene glycol 400) | 5.00 |
| Ethanol | 1.00 |
| (2-O-β-D-Glucopyranosyl)-sn-glycerol | 1.50 |
| Serine | 1.50 |
| Carbomer 2984 | 0.70 |
| Fragrance, preservatives, dyes, antioxidants, etc. | q.s. |
| Water | to 100.00 |

| Example 9: | % by wt. |
|---|---|
| PEG 8 (polyethylene glycol 400) | 5.00 |
| Ethanol | 1.00 |
| (2-O-β-D-Glucopyranosyl)-sn-glycerol | 1.50 |
| Trehalose | 1.50 |
| Carbomer 2984 | 0.70 |
| Fragrance, preservatives, dyes, antioxidants, etc. | q.s. |
| Water | to 100.00 |

| Example 10: | % by wt. |
|---|---|
| PEG 8 (polyethylene glycol 400) | 5.00 |
| Ethanol | 1.00 |
| (2-O-β-D-Glucopyranosyl)-sn-glycerol | 1.50 |
| Glycerol | 1.50 |
| Carbomer 2984 | 0.70 |
| Fragrance, preservatives, dyes, antioxidants | q.s. |
| Water | to 100.00 |

| Example 11: | % by wt. |
|---|---|
| PEG 8 (polyethylene glycol 400) | 5.00 |
| Ethanol | 1.00 |
| (2-O-β-D-Glucopyranosyl)-sn-glycerol | 1.50 |
| Serine | 1.50 |
| Trehalose | 1.50 |
| Carbomer 2984 | 0.70 |
| Fragrance, preservatives, dyes, antioxidants | q.s. |
| Water | to 100.00 |

| Example 12: | % by wt. |
|---|---|
| PEG 8 (polyethylene glycol 400) | 5.00 |
| Ethanol | 1.00 |
| (2-O-β-D-Glucopyranosyl)-sn-glycerol | 1.50 |
| Panthenol | 1.00 |
| Tocopherol acetate | 1.50 |
| Carbomer 2984 | 0.70 |
| Fragrance, preservatives, dyes, antioxidants | q.s. |
| Water | to 100.00 |

| Example 13: | % by wt. |
|---|---|
| PEG 7-hydrogenated castor oil | 4.00 |
| Wool wax alcohol | 1.50 |
| Beeswax | 3.00 |
| Tryglyceride, liquid | 5.00 |
| Petroleum jelly | 9.00 |
| Ozokerite | 4.00 |
| Liquid paraffin, subliquidum | 4.00 |
| (2-O-β-D-Glucopyranosyl)-sn-glycerol | 1.50 |
| Magnesium sulphate.7H$_2$O | 0.70 |
| Fragrance, preservatives, dyes, antioxidants | q.s. |
| Water | to 100.00 |

We claim:

1. A cosmetic or pharmaceutical formulation comprising a pharmaceutically and/or a cosmetically effective amount of (pentosyl) hexosyl ether glycerides and/or (hexosyl) hexosyl ether glycerides, said amount being sufficient to improve moisturization.

2. A cosmetic or pharmaceutical formulation according to claim 1, wherein the hexoses on which said hexosyl glycerides are based are the aldohexoses.

3. A cosmetic or pharmaceutical formulation according to claim 1, wherein the (hexosyl) hexoses on which the hexosyl (hexosyl) glycerides are based are selected from the group consisting of pyranosylpyranoses and furanosylpyranoses having a 1,4-glycosidic or 1,6-glycosidic linkage.

4. A cosmetic or pharmaceutical formulation according to claim 1, wherein the hexoses on which the hexosyl glycerides are based are chosen from the group of pyranosylpyranoses and furanosylpyranoses having a 1,4-glycosidic or 1,6-glycosidic linkage.

5. A cosmetic or pharmaceutical formulation according to claim 1, wherein the hexosyl glycerides are selected from the group consisting of

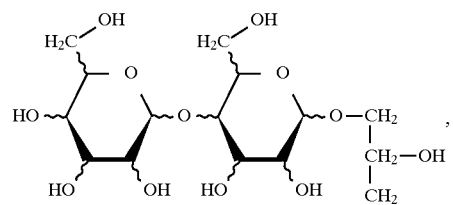

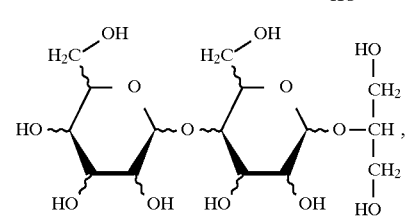

-continued

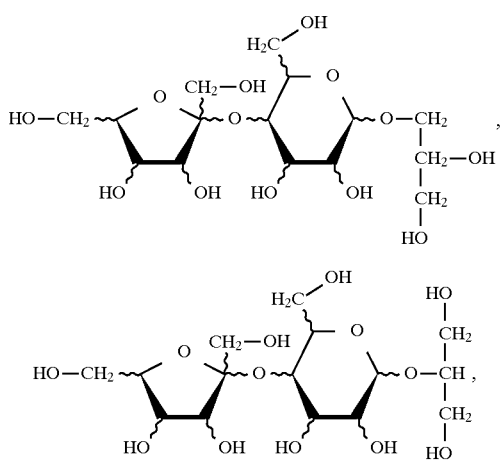

and mixtures thereof.

6. A cosmetic or pharmaceutical formulation according to claim 1, wherein the formulation further comprises an antioxidant.

7. A cosmetic or pharmaceutical formulation according to claim 6, wherein the antioxidant is selected from the group consisting of tocopherol, carotenes and their antioxidant derivatives and mixtures thereof.

8. A cosmetic or pharmaceutical formulation according to claim 6, wherein the antioxidant is present in an amount ranging from 0.05–30%.

9. A cosmetic or pharmaceutical formulation according to claim 1, wherein the formulation further comprises one or more ultraviolet light screening agents.

10. A cosmetic or pharmaceutical formulation according to claim 9, wherein the ultraviolet light screening agents are one or more UVB screening agents.

11. A cosmetic or pharmaceutical formulation according to claim 9, wherein the ultraviolet light screening agents are one or more UVA screening agents.

12. A cosmetic or pharmaceutical formulation comprising a pharmaceutically and/or cosmetically effective amount of hexosyl ether glycerides and/or (hexosyl) hexosyl ether glycerides, said amount being sufficient to improve moisturization.

13. A cosmetic or pharmaceutical formulation according to claim 12, wherein the hexosyl glyceride is (2-O-β-D-glucopyranosyl)-snglycerol.

14. A cosmetic or pharmaceutical formulation comprising from about 0.001 to about 10% by weight (pentosyl) hexosyl ether glycerides and/or (hexosyl) hexosyl ether glycerides, based on the overall weight of the formulation.

15. A cosmetic or pharmaceutical formulation according to claim 14, wherein the formulations comprises from 0.01% by weight to 6% by weight of hexosyl ether glycerides and/or (hexosyl) hexosyl ether glycerides, based on the overall weight of the formulation.

16. A method of increasing the moisture in the skin which comprises applying to the skin an effective amount of a glycosyl glyceride.

* * * * *